(12) United States Patent
Langford (10) Patent No.: US 10,507,341 B2
(45) Date of Patent: Dec. 17, 2019

(54) RESPIRATOR FILTER INTERFACE

(71) Applicant: Scott Health & Safety Limited, Lancashire (GB)

(72) Inventor: Graham Langford, Wirral (GB)

(73) Assignee: Scott Health & Safety Limited (GB)

(*) Notice: Subject to any disclaimer, the term of this patent is extended or adjusted under 35 U.S.C. 154(b) by 1018 days.

(21) Appl. No.: 14/854,328

(22) Filed: Sep. 15, 2015

(65) Prior Publication Data

US 2016/0059049 A1 Mar. 3, 2016

Related U.S. Application Data

(63) Continuation of application No. PCT/GB2014/050782, filed on Mar. 14, 2014.
(Continued)

(30) Foreign Application Priority Data

Jun. 3, 2013 (GB) .................................. 1309930.4

(51) Int. Cl.
*A62B 9/04* (2006.01)
*A61M 16/10* (2006.01)
(Continued)

(52) U.S. Cl.
CPC .............. *A62B 9/04* (2013.01); *A61M 16/00* (2013.01); *A61M 16/06* (2013.01); *A62B 7/00* (2013.01);
(Continued)

(58) Field of Classification Search
CPC ................ A61M 16/06; A61M 16/009; A61M 16/0093; A61M 16/0087; A61M 16/105;
(Continued)

(56) References Cited

U.S. PATENT DOCUMENTS 2,625,155 A * 1/1953 Engelder ............... A61M 16/06
128/206.24
4,433,684 A * 2/1984 Sarnoff ................. A61M 15/00
128/202.15
(Continued)

FOREIGN PATENT DOCUMENTS

| EP | 0 394 139 | 10/1990 |
|----|-----------|---------|
| FR | 871 698 A | 5/1942 |
| WO | 2012/003133 A1 | 5/2012 |

OTHER PUBLICATIONS

International Search Report and Written Opinion of the International Searching Authority dated Dec. 12, 2014 for International Application Serial No. PCT/GB2014/050782, International Filing Date Mar. 14, 2014 consisting of 10-pages.

*Primary Examiner* — Michael J Tsai
(74) *Attorney, Agent, or Firm* — Christopher & Weisberg, P.A.

(57) ABSTRACT

A respiratory inlet having a mask end and a fitting end is provided. The respiratory inlet also includes a cavity and an exterior mating surface. The exterior mating surface is disposed proximate the fitting end, and is configured to matingly accept a first type of air supply fitting. The first type of air supply fitting is configured as a female fitting, and the respiratory inlet is configured to operate in a first mode when the female fitting is mated to the exterior mating surface. The cavity includes an opening oriented toward the fitting end, and an interior mating surface configured to matingly accept a second type of air supply fitting. The second type of air supply fitting is configured as a male fitting, and the respiratory inlet is configured to operate in a second mode when the male fitting is mated to the interior mating surface.

17 Claims, 5 Drawing Sheets

Related U.S. Application Data (60) Provisional application No. 61/793,621, filed on Mar. 15, 2013.

(51) Int. Cl.
 *A61M 16/06* (2006.01)
 *A61M 16/00* (2006.01)
 *A62B 7/00* (2006.01)
 *A62B 9/02* (2006.01)
 *A62B 18/02* (2006.01)
 *A62B 23/02* (2006.01)

(52) U.S. Cl.
 CPC .............. *A62B 9/02* (2013.01); *A62B 18/02* (2013.01); *A62B 23/02* (2013.01); *A61M 16/105* (2013.01)

(58) Field of Classification Search
 CPC ............ A61M 16/1055; A61M 16/106; A61M 16/1065; A61M 16/107; A61M 16/0605; A61M 16/0611; A61M 16/0616; A61M 16/0622; A61M 16/0627; A61M 2016/0661; A62B 7/00; A62B 7/02; A62B 7/04; A62B 7/06; A62B 7/08; A62B 7/10; A62B 7/12; A62B 7/14; A62B 9/04
 USPC ....................................................... 285/324
 See application file for complete search history.

(56) References Cited

U.S. PATENT DOCUMENTS

| | | | | |
|---|---|---|---|---|
| 4,453,544 | A * | 6/1984 | Silverthorn | A62B 18/08 128/206.15 |
| 4,951,661 | A * | 8/1990 | Sladek | A61M 16/0808 128/202.27 |
| 5,701,886 | A * | 12/1997 | Ryatt | A61M 16/06 128/200.14 |
| 5,775,323 | A | 7/1998 | Knott | |
| 6,497,756 | B1 * | 12/2002 | Curado | B01D 53/0415 128/201.25 |
| 6,725,858 | B2 * | 4/2004 | Loescher | A61M 16/08 128/200.14 |
| 7,093,596 | B2 * | 8/2006 | Muller | A62B 23/02 128/202.27 |
| 8,919,368 | B2 * | 12/2014 | Abraham | F16K 13/00 137/15.18 |
| 2004/0025880 | A1 * | 2/2004 | Capon | A62B 9/04 128/206.15 |
| 2005/0102986 | A1 * | 5/2005 | Gosweiler | B01D 46/0058 55/502 |
| 2007/0277829 | A1 * | 12/2007 | Casewell | A62B 18/02 128/206.24 |
| 2008/0156329 | A1 * | 7/2008 | Gerson | A62B 18/025 128/206.12 |
| 2008/0210242 | A1 * | 9/2008 | Burk | A61M 16/06 128/206.21 |
| 2009/0260628 | A1 * | 10/2009 | Flynn, Sr. | A61M 16/0078 128/203.28 |
| 2016/0074683 | A1 * | 3/2016 | Bergeron | A62B 18/08 128/201.19 |

* cited by examiner

RESPIRATOR FILTER INTERFACE

CROSS-REFERENCE TO RELATED APPLICATIONS

This application is a continuation of International Patent Application No. PCT/GB2014/050782 filed Mar. 14, 2014, which claims the benefit of and priority to U.S. Provisional Application No. 61/793,621 filed Mar. 15, 2013, and Great Britain Provisional Application No. 1309930.4 filed Jun. 3, 2013, the contents of each of which are incorporated herein by reference.

The subject matter described herein relates generally to inlets or interfaces for respirators, and particularly to inlet assemblies configured to accept different types of fittings.

BACKGROUND OF THE DISCLOSURE

Conventional respirator assemblies may utilize a mask or face piece configured to fit over the head of a user and/or be worn by a user. Respirator assemblies may include an inlet or inhale port or fitting configured to allow air for breathing into the mask. In some situations, for example, Chemical, Biological, Radiological, and Nuclear (CBRN) defense applications, a wearer or user of a respirator assembly may be required to utilize a Self-Contained Breathing Apparatus (SCBA) during all or a portion of an operation. After the operation is complete, the user may follow a decontamination procedure before entering into a clean environment. Certain current decontamination techniques involve removing a SCBA mask or face piece and fitting an Air-Purifying Respirator (APR) mask or face piece in a controlled manner to avoid contamination and inhalation of possible CBRN substances. During such a switch, operators or users may be subjected to contamination, and may be required to hold their breath and/or close their eyes during the switch. Further, depending on the length of an operation and possibly varying levels of contamination encountered during different portions of the operation, it may be desirable for a wearer or user to switch from use of the SCBA during portions of the operation that are subject to less contamination, in order to conserve an air supply provided by the SCBA. To switch from the SCBA to, for example, respiration using an APR, may require switching masks or face pieces. During such a switch, an operator or user may be subjected to contamination.

Other conventional approaches may require a user to remove or add adaptors or other components to change air sources while wearing a respirator, potentially in a contaminated state. Such removal as conventionally provided may be difficult or inconvenient. For example, certain approaches may require a user to unscrew any air equipment from a mask and replace with clean equipment that is screwed into the mask. During the changing of equipment, the respirator may suffer from ingress of contamination, and users may be required to hold their breath and/or close their eyes. This holding of breath, closing of eyes, or other inconveniences may subject the user to danger from external sources, danger from contamination, and/or increased risk of equipment misuse or damage.

SUMMARY OF THE DISCLOSURE

In various embodiments, a respiratory inlet configured for securement to a mask is provided. The respiratory inlet has a mask end configured to be secured to the mask and a fitting end configured to mate with a supply fitting of an air supply system. The respiratory inlet also includes a cavity and an exterior mating surface. The exterior mating surface is disposed proximate the fitting end, and is configured to matingly accept a first type of air supply fitting. The first type of air supply fitting is configured as a female fitting, and the respiratory inlet is configured to operate in a first mode when the female fitting is mated to the exterior mating surface. The cavity includes an opening oriented toward the fitting end, and includes an interior mating surface configured to matingly accept a second type of air supply fitting. The second type of air supply fitting is configured as a male fitting, and the respiratory inlet is configured to operate in a second mode when the male fitting is mated to the interior mating surface.

In various embodiments, a respiratory inlet assembly configured for securement to a mask is provided. The respiratory inlet assembly includes a respiratory inlet and an adaptor. The respiratory inlet includes a mask end, a fitting end, an exterior mating surface, and a cavity. The mask end is configured to be secured to the mask and the fitting end is configured to mate with a supply fitting of an air supply system. The exterior mating surface is disposed proximate the fitting end and is configured to matingly accept a first type of air supply fitting. The cavity includes an opening oriented toward the fitting end. The cavity also includes an interior mating surface configured to matingly accept a second type of air supply fitting. The adaptor may be formed as a generally annular member, and include an adaptor cavity passing through the adaptor. The exterior mating surface extends circumferentially around the adaptor. The adaptor cavity is configured to matingly accept a third type of air supply fitting. The exterior mating surface shares a common configuration with the second type of air supply fitting, wherein the exterior mating surface of the adaptor is configured for mating engagement with the interior mating surface of the cavity of the respiratory inlet.

In various embodiments, a respiratory assembly including a mask and a respiratory inlet is provided. The mask includes an inlet port, and the respiratory inlet is configured to be accepted by the inlet port. The respiratory inlet has a mask end configured to be secured to the mask and a fitting end configured to mate with a supply fitting of an air supply system. The respiratory inlet also includes a cavity and an exterior mating surface. The exterior mating surface is disposed proximate the fitting end, and is configured to matingly accept a first type of air supply fitting. The first type of air supply fitting is configured as a female fitting, and the respiratory inlet is configured to operate in a first mode when the female fitting is mated to the exterior mating surface. The cavity includes an opening oriented toward the fitting end, and includes an interior mating surface configured to matingly accept a second type of air supply fitting. The second type of air supply fitting is configured as a male fitting, and the respiratory inlet is configured to operate in a second mode when the male fitting is mated to the interior mating surface.

BRIEF DESCRIPTION OF THE DRAWINGS

The drawings, in which like numerals represent similar parts, illustrate generally, by way of example, but not by way of limitation, various embodiments discussed in the present document.

DETAILED DESCRIPTION OF THE DISCLOSURE

Generally, in various embodiments, a multifunctional or multi-mode inlet system may be provided that allows plural modes of air supply to be connected to a respirator. As one example, two different modes of air supply may be provided, or, as another example, three different modes of air supply may be provided. A mode of air supply may be understood as including a specific type of fitting used to provide air from a source to a mask or face piece. Thus, in a system providing for three modes of air supply, three different types of supply fittings may need to be accommodated. By way of example, a first mode of air supply may provide air from an Air Purifying Respirator (APR) that is passed from the environment through a canister filter and into the mask via a first type of fitting. A second mode of air supply may provide air from a Self-Contained Breathing Apparatus (SCBA), for instance via a demand valve having a second type of fitting. A third mode of air supply may provide air from a Powered Air Purifying Respirator (PAPR) that is passed from the environment through a canister filter with the assistance of a fan and into the mask via a third type of fitting.

In various embodiments, an inlet assembly may be configured to accept an APR filter via a first inlet mating portion. The first inlet mating portion may be configured as an external mating surface configured to accept a female mating fitting of the APR filter. Also, the inlet assembly may be configured to accept a SCBA demand valve via a second inlet mating portion. The second inlet mating portion may be configured as an interior surface of a cavity (or an interior surface of an adaptor secured in the cavity) configured to accept a male mating fitting of the SCBA demand valve. Further, the inlet assembly may be configured to accept a PAPR filter via a third inlet mating portion. The third inlet mating portion may be configured as an interior surface of a cavity configured to accept a male mating fitting of the PAPR. For example, the PAPR may include a NATO DIN40 thread that is accepted by a corresponding NATO DIN40 thread formed on an interior surface of the cavity. It may be noted that a non-powered APR may also include a male fitting, such as a male fitting including a NATO DIN40 thread, so that different types of APRs or other filters may be accepted by the inlet assembly (e.g., a first type of filter via the first inlet mating portion and a second type of filter via the third inlet mating portion).

As mentioned above, the inlet assembly may be configured to provide for the supply of air from an APR filter canister into a mask or face piece of a respirator in the first mode of operation. The APR filter canister may be, for example, configured for use for military applications. The inlet assembly may include a shut-off structure, and a shut-off insert may include a cooperating automatic shut-off structure, with the shut-off structures configured to prevent ingress of air and/or contaminants from entering the mask once the filter canister is disconnected from the mask. For example, the APR filter canister may include a female fitting configured to accept an external surface of the inlet assembly and a male automatic shut-off feature that is internally accepted by the shut-off structure of the shut-off insert. The shut-off insert may be releasably securable to the inlet assembly. Components that are described herein as "releasably securable" or "releasably secured" may be understood as being configured for non-destructive removal and re-attachment. Thus, "releasably securable" or "releasably secured" components may be removed or replaced without loss of functionality or need of repair after removal and re-attachment, or remain fully functional for an original intended purpose or purposes after removal and/or replacement. When the shut-off insert is in place, the inlet assembly may provide for automatic shut-off, but when the shut-off insert is removed, the inlet assembly may not provide automatic shut-off, but may be able to accept additional different types of fittings in the cavity that would otherwise be blocked by the shut-off insert. The mask may be configured to accept two canister filters, one at each of two separate inlets, with a user able to change the canister filters one at a time, helping to prevent entry of contamination while still providing for the supply of air during a change of canister filters.

The inlet assembly may further be configured to provide for the supply of air from a SCBA system (e.g., via a demand valve of the SCBA system). For example, the shut-off insert may be removed, clearing a cavity of the inlet assembly for use in a second mode of operation, in which a cavity of the inlet assembly previously occupied by the shut-off insert may accept a male fitting of a demand valve of a SCBA. It may be noted that, in applications utilizing two or more inlet ports, ingress of contaminants into the mask during insertion or removal of the demand valve fitting may be inhibited or prevented by a silicone valve associated with the inlet assembly from which the demand valve is being removed (or into which the demand valve is being inserted) by using positive pressure applied at a different port of the mask (e.g., positive pressure from a PAPR).

In various embodiments, the cavity of the inlet assembly may be configured to accept a ring-shaped adapter that includes a cavity that accepts the shut-off insert and/or the male fitting employed during the second mode of operation. Removal of the ring-shaped adapter thus may reveal an interior surface of the cavity of the inlet assembly. The interior surface of the cavity of the inlet assembly may be configured to accept a third type of fitting for use in a third mode of operation. For example, the third type of fitting may be a male fitting of a PAPR or APR filter canister of a different type than the filter canister used in the first mode of operation. In various embodiments, the third type of fitting may include a male fitting configured as a NATO DIN40 thread. It may be noted that the female thread for the first mode of operation may fit around an outside of the inlet assembly, such that the inlet assembly may be used in the first mode of operation irrespective of whether the shut-off insert and/or adaptor are in place in the cavity of the inlet assembly.

Thus various embodiments provide a modular inlet assembly allowing for convenient switching between various modes of operation or types of fittings of air supply systems. The types of fittings may differ in size and/or configuration. A technical effect of various embodiments includes improved convenience in switching between modes or types of air supply during a mission and/or decontamination (e.g., avoiding the removal of a mask, the holding of breath, and/or the closing of eyes). A technical effect of various embodiments includes reduction in the ingress of air or potential contaminants into a mask during switching of modes or types of air supply. A technical effect of various embodiments includes improved safety and versatility of respirator systems for CBRN or other hazardous applications.

Figure 1:
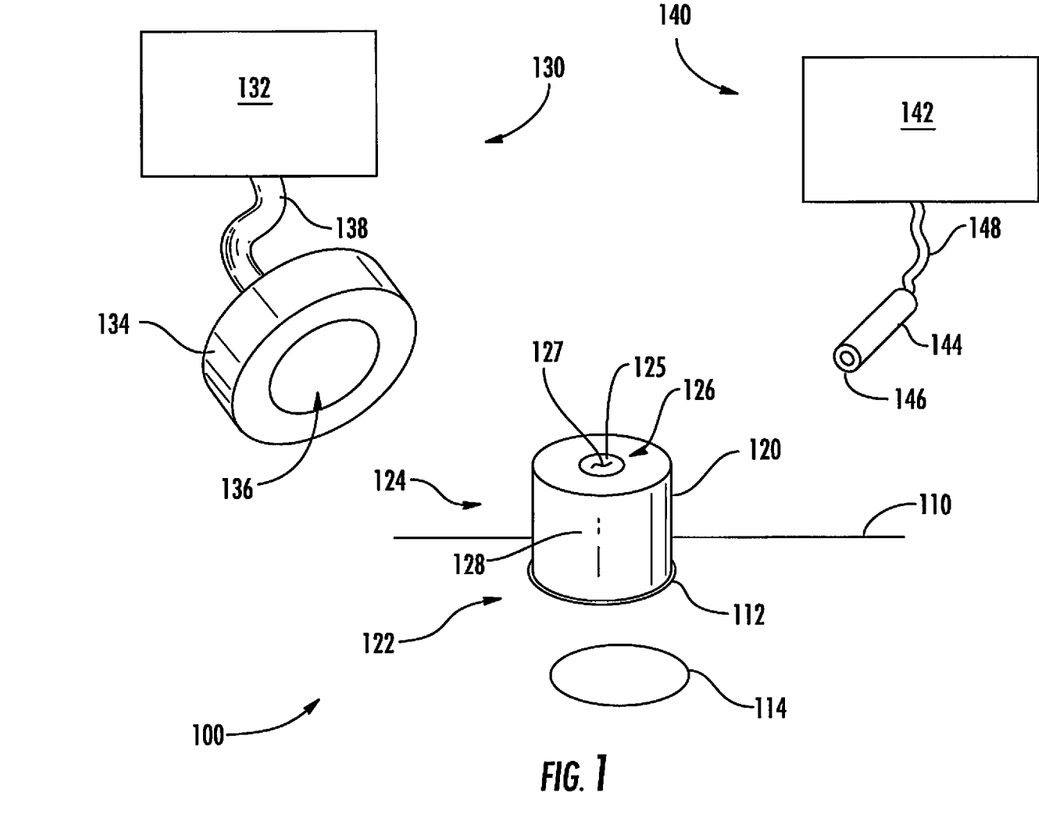
FIG. 1 is a schematic view of a respirator system formed in accordance with various embodiments.

FIG. 1 is a schematic view of a respirator system 100 formed in accordance with various embodiments. The respirator system 100 include a mask 110 and a respiratory inlet 120 configured for interchangeable operation with a first air supply system 130 and a second air supply system 140. Generally in various embodiments, the respiratory inlet 120 is configured to allow supply of air from an air supply system (e.g., first air supply system 130, second air supply system 140) into the mask 110.

An air supply system as used herein may be understood as a system or group of components configured for the provision of air for breathing to a mask, face piece, or the like worn or utilized by an operator or user. Examples of air supply systems include APR or other filter canister systems, PAPR systems, or SCBA systems, among others. An air supply system may actively provide air, for example via a fan or pressurized device that delivers air into the mask. Other air supply systems may passively provide air, for example via air drawn in from the atmosphere through a filter by the unaided breathing of a wearer of the mask. Various air supply systems may be configured for positive pressure operation, wherein a positive pressure is maintained inside the confines of a mask, hood, or the like worn by a user. Other air supply systems may be configured for negative pressure operation, where a positive pressure is not maintained inside the mask and air is drawn from the outside by the unaided breathing of a user.

The mask 110 is configured to be worn by an operator or user. In various embodiments, the mask 110 may include one or more of a face shield, a hood, a head sock, or the like. Generally, the mask 110 is configured to protect the user from contaminants in the atmosphere or surroundings that may be encountered by the user, while permitting the user to see out of the mask 110. In the illustrated embodiment, the mask 110 includes an inlet port 112 and an outlet port 114. The inlet port 112 is configured for mounting the respiratory inlet 120, and the outlet port 114 is configured for mounting a respiratory outlet (not shown in FIG. 1 for clarity and simplicity of illustration). The inlet port 112 and the outlet port 114 may be configured to accept the respiratory inlet 120 and respiratory outlet, respectively, in an airtight fashion, to inhibit or prevent leakage of air into or out of the mask 110 that is not controlled via the respiratory inlet 120 or the respiratory outlet. It should be noted that different numbers or types of ports may be employed in alternate embodiments. For example, in some embodiments, two inlet ports may be employed, with each inlet port accepting a separate respiratory inlet, allowing for plural air supply systems to be employed (e.g., one air supply system per respiratory inlet/inlet port). As another example, in some embodiments, a communication port for communication equipment may be provided. As one more example, in various embodiments, a combined inlet/outlet port may be used for a combination respiratory inlet/outlet.

The respiratory inlet 120 is configured to connect the interior of the mask 110 in fluid communication with an air supply system. Thus, the respiratory inlet 120 may include a central pathway or corridor passing therethrough to provide a pathway for air from an air supply system into the mask 110. One or more valves, shut-off mechanisms, or the like may be disposed along the pathway to control the flow of air into or out of the mask 110.

In the illustrated embodiment, the respiratory inlet includes a mask end 122 and a fitting end 124. The mask end 122 is configured to be oriented toward and secured to the mask 110 in a generally air tight fashion. For example, the mask end 122 may include a male thread surrounding a central passageway that is inserted into the mask 110, with a threaded nut on the inside of the mask 110 used to secure the respiratory inlet 120 to the mask 110. One or more gaskets or the like may be employed to prevent or inhibit air leakage where the respiratory inlet 120 joins the mask 110. In other embodiments, other connectors or joining techniques may be used to join the respiratory inlet 120 to the mask 110. The fitting end 124 is disposed opposite the mask end 122. The fitting end 124 is configured to matingly engage a fitting of an air supply system in a generally air tight fashion to allow the provision of air from the air supply system into the respiratory inlet 120, and the passage of air through the respiratory inlet 120 to the interior of the mask 110. In various embodiments, the fitting end 124 may be understood as being positioned at a surface or edge of the respiratory inlet 120 nearest a fitting to be mated with the respiratory inlet and/or at a contact point or line where the fitting and the respiratory inlet meet, and extending along a length of a mating contact or surface between the fitting and the respiratory inlet 120.

The depicted respiratory inlet 120 includes a cavity 126 having an opening 125 at the fitting end 124 that is oriented toward a fitting of an air supply system to be accepted by the respiratory inlet 120. The cavity 126 extends inwardly into the respiratory inlet 120 from the opening 125 at the fitting end 124, and includes an internal mating surface 127. The internal mating surface 127 is configured as a female mating surface configured to accept a male mating surface of an air supply fitting. The internal mating surface 127 may include one or more of a taper, threads, guides, or securement features configured to accept and/or secure a male air supply fitting to the respiratory inlet 120. Once a male air supply fitting is secured to the internal mating surface 127, air may be supplied to the mask 110 through the respiratory inlet 120.

The depicted respiratory inlet 120 also includes an exterior mating surface 128. In the illustrated embodiment, at least a portion of the exterior mating surface 128 is disposed proximate the fitting end 124. The exterior mating surface 128 is configured as a male mating surface configured to accept a female mating surface of an air supply fitting. The exterior mating surface 128 may include one or more of a taper, threads, guides, or securement features configured to accept and/or secure a female air supply fitting to the respiratory inlet 120. Once a female air supply fitting is secured to the exterior mating surface 128, air may be supplied to the mask 110 through the respiratory inlet 120. Thus, a first type of air supply system having a female fitting may be accepted by the exterior mating surface 128 allowing for operation in a mode corresponding to the first type of air supply system, while a different, second type of air supply system having a male fitting may be accepted by the interior mating surface 127 of the cavity 126, allowing for operation in a different mode corresponding to the different, second type of air supply system.

The first air supply system 130 depicted in FIG. 1 is configured with a female fitting sized and configured to be accepted by the exterior mating surface 128 of the respiratory inlet 120. In the illustrated embodiment, the first air supply system 130 includes a first air supply 132 and a first fitting 134 having a first fitting cavity 136. The first fitting cavity 136 is configured to matingly join the exterior mating surface 128 of the respiratory inlet 120, such that the respiratory inlet 120 and the first air supply 132 are placed in a substantially air tight fluid communication. In the illustrated embodiment, the first air supply system 132 is depicted as having a conduit 138 joining the first air supply 132 to the first fitting 134; however, in other embodiments the first fitting 134 may be directly or integrally joined to the first air supply 132. By way of example, the first air supply system 130 may be configured as an APR with the first air supply 132 including a canister filter. As another example, the first air supply system 130 may be configured as a PAPR with the first air supply filter 132 including a canister filter and a fan or other device for driving or assisting the flow of air through the canister filter. As yet one more example, the first air supply system 130 may be configured as a SCBA with a pressurized tank configured to deliver air to the respiratory inlet 120.

The depicted second air supply system 140 is configured with a male fitting sized and configured to be accepted by the internal mating surface 127 of the cavity 126 of the respiratory inlet 120. In the illustrated embodiment, the second air supply system 140 includes a second air supply 142 and a second fitting 144 having a second fitting male end 146. The second fitting male end 146 is configured to matingly join the internal mating surface 127 of the cavity 126 of the respiratory inlet 120, such that the respiratory inlet 120 and the second air supply 142 are placed in a substantially air tight fluid communication. In the illustrated embodiment, the second air supply system 142 is depicted as having a conduit 148 joining the second air supply 142 to the second fitting 144. In various embodiments, however, the second fitting 144 may be directly or integrally joined to the second air supply 142. The second air supply system 140 in various embodiments may, for example, be configured as an APR, PAPR, or SCBA system as discussed herein. Generally, the first fitting cavity 136 of the first fitting 134 and the second fitting male end 146 of the second fitting 144 may be sized and configured so that the first fitting cavity 136 is large enough relative to the second fitting male end 146 so that the respiratory inlet 120 may have a cavity large enough to accept the second fitting male end 146 while still having an outer dimension small enough to be accepted by the first fitting cavity 136.

The second air supply system 140 may be configured as a different type of system than the first air supply system 130. As just one example, the first air supply system 130 may be configured as an APR system, with the respirator assembly 100 configured to operate in a first mode of APR operation when the first air supply system 130 is operably connected to the mask 110 via the respiratory inlet 120, while the second air supply system 140 may be configured as a SCBA system, with the respirator assembly 100 configured to operate in a second mode of SCBA operation when the second air supply system 140 is operably connected to the mask 110 via the respiratory inlet 120. To switch from APR operation to SCBA operation, the user may disconnect and remove the first fitting 134 from the fitting end 124 of the respiratory inlet 120, and connect the second fitting 144 to the fitting end 124 of the respiratory inlet 120. Switching between air supply types or modes of operations as provided by various embodiments (e.g., respiratory assembly 100) thus eliminates or minimizes changing of the mask or performance of other inconvenient or dangerous manipulations, and allows for quick, reliable switching between modes of operation while eliminating, minimizing, or reducing risk of exposure to contaminants during the switch between air supply types or modes of operation.

Thus, in the illustrated embodiment, the respiratory inlet 120 allows for convenient switching between modes, with no modifications, alterations, adjustments, to the respiratory inlet required. In FIG. 1 two different modes of operation are depicted; however, more modes of operation may be provided for in other embodiments. For example, inserts and/or adaptors may be provided to provide additional functionality or flexibility, such as use of additional modes having additional types of fittings.

Figure 2:
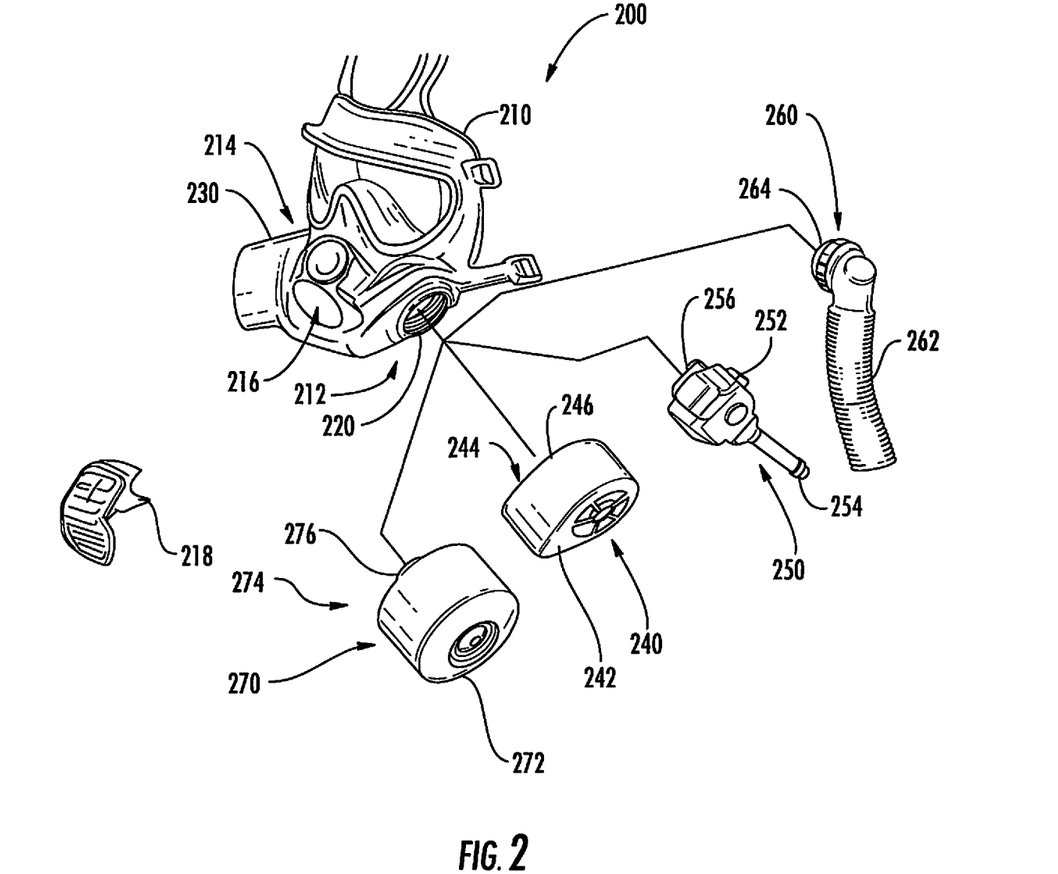
FIG. 2 is perspective view of a respirator system formed in accordance with various embodiments.

FIG. 2 is perspective view of a respirator system 200 formed in accordance with various embodiments. The respirator system 200 includes a mask 210, a first fitting inlet 220, and a second fitting inlet 230. The respirator system 200 is configured to receive a supply of air via one or more of a first supply system 240, a second supply system 250, a third supply system 260, and a fourth supply system 270. The respirator system 200 is configured to allow for quick, reliable switching between types of air supply or modes of operation during an operation or during cleaning or decontamination. As one example, a user may use air provided from a SCBA air supply during a portion of an operation subject to relatively high levels of contamination, and switch to an APR air supply during a portion of an operation having relatively low levels of contamination, thereby preserving an air supply stored in a tank of a SCBA.

The mask 210 may be configured generally similarly in respects to the mask 110 discussed in connection with FIG. 1. As shown in FIG. 2, the mask 210 includes a first inlet port 212, a second inlet port 214, and an outlet port 216. A respiratory outlet 218 is shown in FIG. 2 that is releasably securable to the outlet port 216. Also, in FIG. 2, an APR canister is shown releasably secured to the second fitting inlet 230, while no air supply is shown operably connected to the first fitting inlet 220. The use of two inlets allow for an air supply associated with one inlet to be used while an air supply associated with the other inlet is switched. The use of two inlets also allows for the use of two air supplies concurrently or simultaneously. For example, two air supply systems (either of similar or different type) may be attached to the mask 210 and alternated between. An air supply may be switched, for example, to replace an expended filter canister, or as another example, to switch between modes of operation based on a changing level of contamination encountered during an operation.

The first fitting inlet 220 and the second fitting inlet 230 may be configured generally similarly in certain respects to the respiratory inlet 120 discussed herein. Additional details of an example respiratory inlet assembly including structures, aspects, or features that may be employed by the first fitting inlet 220 and/or the second fitting inlet 230 are provided in FIGS. 3-6 and the related discussion. In the illustrated embodiment, the first fitting inlet 220 is shown secured to the first inlet port 212, and the second fitting inlet 230 is shown secured to the second inlet port 212.

The depicted first supply system 240 is configured as an APR system. In an APR system, air supplied from the surrounding atmosphere may be drawn by a user's inhalation through a filter canister worn on or attached to the mask via an inlet and/or port. The first supply system 240 includes a filter canister 242 with a fitting end 244 including a first type of fitting 246. The first type of fitting 246 may be a female fitting configured to be accepted by an exterior mounting portion of the first fitting inlet 220 or the second fitting inlet 230, generally similar in certain respects to the first fitting 134 of the first air supply system 130 discussed in connection with FIG. 1. The first type of fitting 246 may be configured to accept an exterior mating surface of one of the first fitting inlet 220 or the second fitting inlet 230. Further, the first type of fitting 246 may include a male portion centrally disposed within a female fitting, with the male portion configured to cooperate with an automatic shut-off insert (see, e.g., FIG. 5 and related discussion). The first supply system 240 may be mounted to one of the first respiratory inlet 220 or the second respiratory inlet 230 for operation of the respiratory system 200 in a first mode of operation (e.g., APR operation).

The second supply system 250 is configured as a SCBA system. In a SCBA system, pressurized air is supplied from a tank that may, for example, be worn by an operator via a belt, harness, or the like. The air is provided from the tank to the mask via a hose or similar conduit. In the illustrated embodiment, the second supply system 250 includes a demand valve 252 operably connected to a tank (not shown) via a hose 254. The demand valve 252 may be configured to provide air from the tank responsive to the breath of the user. For example, a user may inhale to provide a suction pressure above a threshold that activates the supply of air via the demand valve 252. The demand valve 252 includes a second type of fitting 256. The second type of fitting 256 may be generally similar in certain respects to the second fitting 144 discussed in connection with FIG. 1. The second type of fitting 256 may be configured to be accepted by a cavity of one of the first fitting inlet 220 or the second fitting inlet 230, or by a cavity of an adaptor that is secured in one of the fitting inlets. (For an example embodiment of an adaptor, see FIG. 4 and related discussion.) The second supply system 240 may be mounted to one of the first respiratory inlet 220 or the second respiratory inlet 230 for operation of the respiratory system 200 in a second mode of operation (e.g., SCBA operation).

The third supply system 260 is configured as a PAPR system. In a PAPR system, air from the atmosphere is provided to a user through a filter canister, with the flow of air driven or assisted by a fan or other device. In some embodiments, the fan or other device, as well as the filter canister, may be provided on a belt or harness assembly worn by a user, with a hose terminating in a fitting leading from the fan and filter canister assembly to the mask. The depicted third supply system 260 includes a hose 262 that is operably connected to a fan and filter canister assembly (not shown), with the hose terminating in a third type of fitting 264. The third type of fitting 264 may be generally similar in certain respects to the second fitting 144 discussed in connection with FIG. 1. The third type of fitting 264 may be of a different size than the second type of fitting 256. For example, in some embodiments, the third type of fitting 264 may be configured to be accepted by a cavity of one of the first fitting inlet 220 or the second fitting inlet 230, while the second type of fitting 256 may be configured to be accepted by a cavity of an adaptor that is secured in one of the fitting inlets. In some embodiments, the third type of fitting 264 may include a male NATO DIN40 thread. The third supply system 260 may be mounted to one of the first respiratory inlet 220 or the second respiratory inlet 230 for operation of the respiratory system 200 in a third mode of operation (e.g., PAPR operation).

The fourth supply system 270 is configured as an APR system, and may be generally similar to the first supply system 240 discussed herein. The depicted fourth supply system 270, however, uses a different fitting and filter canister than the first supply system 240. The different types of filter canister may be more appropriate or useful for a different type of environment encountered, and/or one may be a readily available standard part while the other may be a less readily available part. The fourth supply system 270 includes a canister filter 272 with a fitting end 274 including a fourth type of fitting 276. In contrast to the fitting of the first supply system 270, the fourth type of fitting 276 may be a male fitting. In some embodiments, the fourth type of fitting 276 may share a configuration with one of the second type of fitting 256 or third type of fitting 264. For example, like the third type of fitting 264, the fourth type of fitting 276 in some embodiments may include a male NATO DIN40 thread. The fourth supply system 270 may be mounted to one of the first respiratory inlet 220 or the second respiratory inlet 230 for operation of the respiratory system 200 in a fourth mode of operation (e.g., a second type of APR operation, different than the first mode associated with the first supply system 240). Thus, the third and fourth modes provide an example of two modes of operation that use a common fitting type for different types of air supply.

FIGS. 3-6 provide various views of a respiratory inlet assembly 300 and various components or aspects thereof formed in accordance with various embodiments. In some embodiments, the respiratory inlet assembly 300 may be used in conjunction with one or more of the air supply systems discussed herein in connection with FIG. 2 and the related discussion. The respiratory inlet assembly 300 is configured for securement to a mask or face piece, and to accept a fitting of an air supply system for the provision of air into the mask or face piece. The respiratory assembly 300 (see FIG. 6) has a mask end 301 and a fitting end 302. The respiratory inlet assembly 300 includes an outer housing 310, an adaptor 330, and an auto shut-off insert 340. The various components of the respiratory inlet assembly 300 may be arranged, combined, and/or utilized as appropriate to allow different types of fittings to be used to provide a flow of air through the respiratory inlet assembly into a mask or face piece. The adaptor 330 is releasably securable to the outer housing 310 and is configured to provide for switching between different types of male supply fittings. In the illustrated embodiment, the shut-off insert 340 is releasably securable to the adaptor 330 and is configured to help prevent the ingress of contaminants when, for example, an APR canister system configured for mating with an exterior surface of the outer housing 310 is disconnected from the respiratory inlet assembly 300. In other embodiments, an alternate or additional shut-off insert 340 that is releasably securable to a cavity of the outer housing 310 may be provided for use when the adaptor 330 is not disposed in the outer housing 310.

Figure 3:
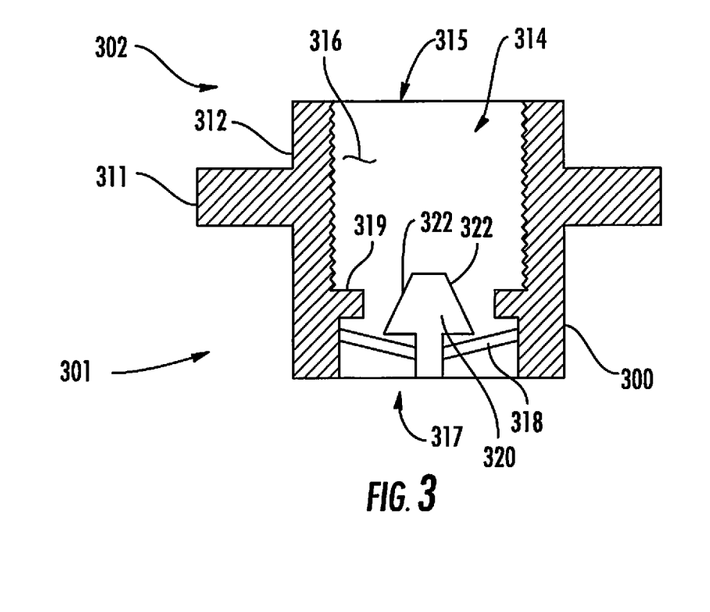
FIG. 3 is a side sectional view of a respiratory inlet formed in accordance with various embodiments.

FIG. 3 is a side sectional view of an outer housing 310 of the respiratory inlet assembly 300 formed in accordance with various embodiments. The outer housing 310 is configured as the main body of the respiratory inlet assembly 300. The outer housing 310 may be understood as an example of a respiratory inlet or respiratory inlet apparatus, as the outer housing 310 is configured to be functional as an inlet in at least one mode without the other components depicted in FIGS. 3-6 (e.g., the outer housing 310 may operate in at least one mode of operation without the adaptor 330 or the shut-off insert 340). The outer housing 310 is generally cylindrical in shape about a central axis, and is configured for a generally air tight connection to a mask. For example, a portion of the exterior of the outer housing 310 proximate the mask end 301 may include a threaded portion (not shown) configured to be accepted by a threaded nut for securement to the mask. The depicted outer housing 310 or respiratory inlet includes a flange 311, an exterior mating surface 312, a cavity 314, a passageway 317, an intake valve 318, and a shut-off member 320. The flange 311 may provide one or more support or guide surfaces for a mask and/or supply fitting. For example, a surface of the flange 311 oriented toward the fitting end 302 may support or position a female fitting placed over the outer housing 310, while a surface of the flange 311 oriented toward the mask end 301 may support or position the outer housing 310 relative to a mask to which the outer housing 310 is secured.

The exterior mating surface 312 is configured as a male fitting surface and is configured to matingly accept a female fitting of an air supply system. For example, the exterior mating surface 312 may be sized and configured to accept the first type of fitting 246 of the APR supply system discussed in connection with FIG. 2. In various embodiments, the exterior mating surface 312 may include one or more of a taper, threads, guides, or securement features configured to accept and/or secure a female air supply fitting to the respiratory inlet assembly 300.

The cavity 314 is generally circular in cross-section about a central axis of the outer housing 310. The cavity 314 includes an opening 315 proximate the fitting end 302, and extends into the outer housing 310 to a surface 319. The cavity 314 also includes an interior mating surface 316. In the illustrated embodiment, the interior mating surface 316 extends circumferentially around an interior portion of the outer housing 310, and the exterior mating surface 312 extends circumferentially around an exterior portion of the outer housing 310, with the interior mating surface 316 and the exterior mating surface 312 disposed concentrically about a central axis of the outer housing 310. In the illustrated embodiment, the interior mating surface 316 is configured to releasably accept or secure the adaptor 330 (e.g., for use of a first size of male fitting), or to matingly accept a second size of male fitting that is larger than first size, depending on the mode of operation or type of air supply fitting being utilized. In various embodiments, the interior mating surface 316 may include one or more of a taper, threads, guides, or securement features. In some embodiments, the adaptor 330 and the male fitting accepted by the interior mating surface 316 may mate or secure to the interior mating surface 316 using a common or shared configuration such as a standard thread. For example, the interior mating surface 316 may be configured as a female NATO DIN40 thread, with the adaptor 330 and male fitting accepted by the interior mating surface including a male NATO DIN40 thread. In some embodiments, the cavity 314 may also accept an automatic shut-off insert sized differently than the shut-off insert 340 accepted by the adaptor 330 of the illustrated embodiment.

The depicted passageway 317 extends from the cavity 314 through the outer housing 310 and provides a pathway for air to pass through the respiratory inlet assembly 300 to a mask to which the respiratory inlet assembly 300 is mounted, affixed, or secured. One or more of a valve or shut-off assembly may be disposed along or proximate the passageway 317 to control the flow of air through the passageway 317. In the illustrated embodiment, the intake valve 318 is disposed along the passageway proximate the mask end 301. The intake valve may be constructed of a flexibly resilient material, such as silicone rubber, and configured to be biasable between a closed position to prevent flow into a mask (e.g., by a positive pressure in the mask provided via a different inlet) and an open position to allow air through (e.g., by a suction force applied by inhaling).

The shut-off member 320 includes a shut-off surface 322. In the illustrated embodiment, the shut-off member 320 is configured as a generally cone shaped structure extending along a central axis of the outer housing 310 along the passageway 317 from the mask end 301 toward the fitting end 302 along central axis through passageway 317. The shut-off member is configured to cooperate with the shut-off insert 340 to provide for shut-off capability by blocking flow through the passageway 317 when the shut-off surface 324 is brought into contact with a surface of the shut-off insert 340. Thus, a surface of the shut-off insert 340 may be brought into a generally air tight contact with the shut-off surface 322 to prevent or inhibit air flow through the passageway 317, and removed from contact to allow air flow through the passageway 317.

Figure 4:
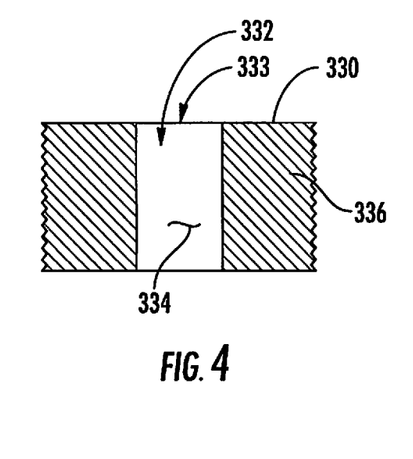
FIG. 4 is a side sectional view of an adaptor formed in accordance with various embodiments.

FIG. 4 is a side sectional view of the adaptor 330. The adaptor 330 is configured to be accepted by the cavity 314 and in turn to accept a male supply fitting that is smaller than male supply fitting accepted by the cavity 314. The adaptor 330 is also configured to accept and releasably secure the shut-off insert 340. In the illustrated embodiment, the adaptor 330 is sized and configured for fitment beneath a top surface of the outer housing 310 when secured to the outer housing 310, or otherwise configured to not interfere with the use of a female fitting (e.g., the first type of fitting 346 of the first air supply system 340 or the first fitting 134) with the exterior mating surface 312. The adaptor 330, due to the relatively compact size, may be made of higher density or stronger or more durable material than may be used for a larger adaptor that extends above or substantially above the outer housing 310.

The depicted adaptor 330 includes a cavity 332 having an opening 333 that extends through the adaptor 330, with the adaptor thus substantially annular or ring-shaped. The sides of the adaptor 330 are shown as generally straight in FIG. 3; however, it should be noted that the interior or the exterior of the adaptor 330 may be sloped or tapered. The cavity 332 includes an adaptor interior mating surface 334 configured to accept a male fitting. The adaptor interior mating insert 334 may include one or more of a taper, threads, guides, or securement features. Further, the cavity 332 of the adaptor 330 is configured to accept the shut-off insert 340. For example, the shut-off insert 340 may be releasably secured in the cavity 332 via one or more of clips, lugs, latches, tabs, slots, grooves, or the like. The adaptor 330 also includes an adaptor exterior mating surface 336 that extends circumferentially around the adaptor 330. The exterior mating surface 336 is configured to be accepted by and releasably securable to the interior mating surface 316 of the cavity 314 outer housing 310. For example, the exterior mating surface 336 may include a male NATO DIN40 thread accepted by a female NATO DIN40 thread of the interior mating surface 316 of the cavity 314 of the outer housing 310. Other configurations may be used to releasably secure the exterior mating surface 336 of the adaptor to the interior mating surface 316 in other embodiments.

Figure 5:
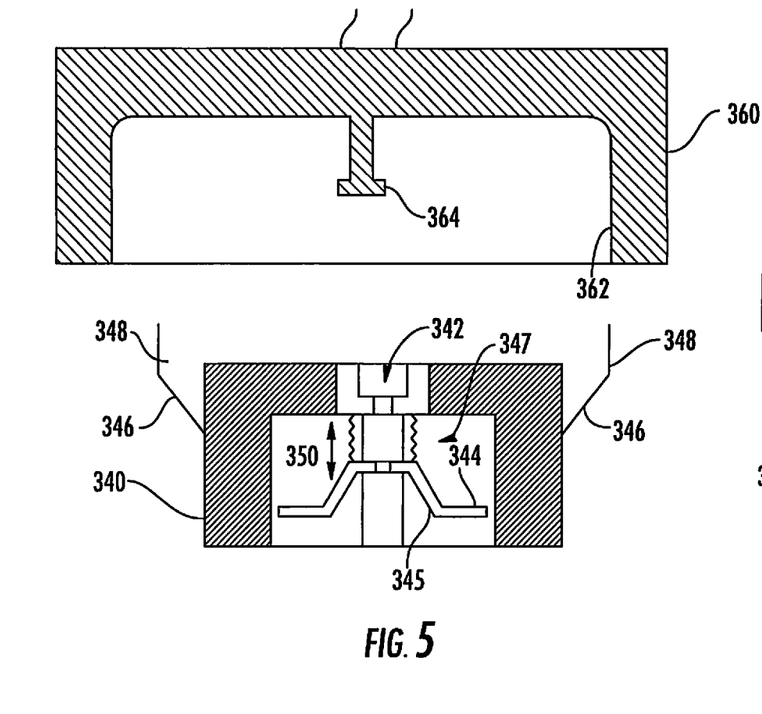
FIG. 5 is a side sectional view of a shut-off insert formed in accordance with various embodiments.

It may be noted that, in various embodiments, an air supply fitting may have aspects that are accepted both internally and externally by the respiratory inlet assembly 300, such as a female fitting that accepts the exterior mating surface 312, and a male auto-shut off feature accepted by a cavity of a shut-off insert disposed within the adaptor 330 and/or the cavity 314 of the outer housing 310. FIG. 5 is a side sectional view of the shut-off insert 340. The shut-off insert 340 is configured to cooperate with the shut-off member 320 of the outer housing 310 to inhibit or prevent the flow of air when the shut-off insert is in place and an air supply fitting is not attached to the outer housing 310. In various embodiments, when an air supply fitting is secured to the exterior mating surface 312 of the respiratory inlet assembly 300 (e.g., via a rotational movement), the rotation of the air supply fitting may also rotate or otherwise actuate an auto-shut-off mechanism of the shut-off insert 340 from a closed position to an open position (e.g., via a cam mechanism), thereby allowing flow through the respiratory inlet. When the air supply fitting is removed, the auto-shut-off mechanism may automatically return to the closed position, preventing or inhibiting flow through the respiratory inlet.

The depicted shut-off insert 340 is generally cylindrically shaped and includes a latch member 346 including a handle 348 configured to releasably secure the shut-off insert 340 to the interior of the adaptor cavity 332. In the illustrated embodiment, two latch members 346 are disposed on opposite sides of the shut-off insert. The handles 348 are configured to provide a convenient surface for grasping and/or actuating the latch members 346. The latch member 346 is resiliently biasable, and extends outwardly from the center of the shut-off insert 340 to an outer dimension that is greater than a diameter of the adaptor cavity 332, such that the latch members 346 are urged inwardly when the shut-off insert 340 is inserted into the adaptor cavity 332. The resiliency of the latch members 346 thus urges the latch members 346 against the adaptor cavity 332 to help retain the shut-off insert 340 in place. The latch members 346 or other feature of the shut-off insert may also cooperate with groove, slot or the like to retain the shut-off insert 340 in a desired position and/or orientation. To remove the shut-off insert 340, the latch members 346 may be biased inwardly (e.g., by applying force to the handles 348) to release the latch members 346 from contact with the adaptor cavity 332. Other securement configurations may be utilized in various embodiments. For example, one or more of a clip, lug, guide, tab, groove, or the like may be employed. The depicted embodiment may be placed and removed axially from the adaptor cavity 332; however, in other embodiments, a shut-off insert may be placed or removed rotationally. It should also be noted that while the depicted shut-off insert 340 as shown is configured to be accepted by adaptor 330, an additional or alternate shut-off insert 340 may be accepted by the cavity 314 of the outer housing 310.

The depicted shut-off insert 340 includes a shut-off opening 342 configured to accept a portion of a supply fitting for actuation of a shut-off mechanism. For example, a supply fitting 360 configured to mate with the respiratory inlet assembly 330 may include a female portion 362 configured to mate with the exterior mating surface 312 and a male portion 364 configured to be accepted by the shut-off opening 342. When the supply fitting 360 is attached to the respiratory inlet assembly 300, the male portion 364 is accepted by the opening 342 and cooperates with the opening 342 to actuate shut-off mechanism from a closed to an open position to permit the flow of air through the respirator inlet.

In the illustrated embodiment, the shut-off inlet includes a shut-off member 344 including a shut-off surface 345 configured to cooperate with the shut-off surface 322 of the shut-off member 320 of the outer housing 310. The shut-off member 344 is actuated by movement (e.g., rotation) of the supply fitting 360 when the supply fitting is engaged with the shut-off opening 342 to move in an actuation direction 350 that is parallel to central axis of outer housing 310. In the illustrated embodiment, a shut-off assembly 347 including the shut-off member 344 is shown schematically for clarity of illustration. Generally, one or more of spring or other resilient structure may be used to maintain the shut-off member 344 in a closed position, while a lever, cam, or the like may be employed upon engagement with the supply fitting 360 to actuate the shut-off member 344 against the spring or other resilient structure to an open position.

Figure 6:
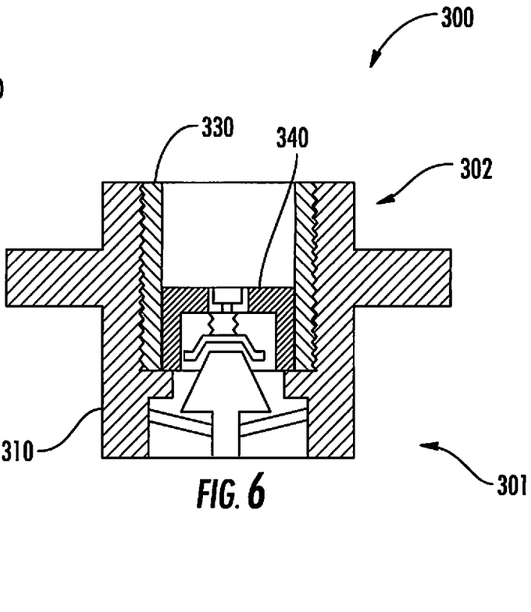
FIG. 6 is a side sectional view of a respiratory inlet assembly formed in accordance with various embodiments.

FIG. 6 is a side sectional view of the respiratory inlet assembly 300. In FIG. 6, the respiratory inlet assembly 300 is shown with the adaptor 330 releasably secured to the outer housing 310, and with the shut-off insert releasably secured to the adaptor cavity 332 of the adaptor 330. In this configuration or mode, the respiratory inlet 300 may accept a female supply fitting with the exterior mating surface 312. For example, the respiratory inlet 300 may accept the supply fitting 360 which also includes the male portion 364 accepted by the shut-off insert 340. Because the adaptor 330 is positioned beneath the top of the outer housing 310, the adaptor 330 does not interfere with the attachment of the supply fitting 360. Various other configurations or modes may also be utilized.

Figure 7:
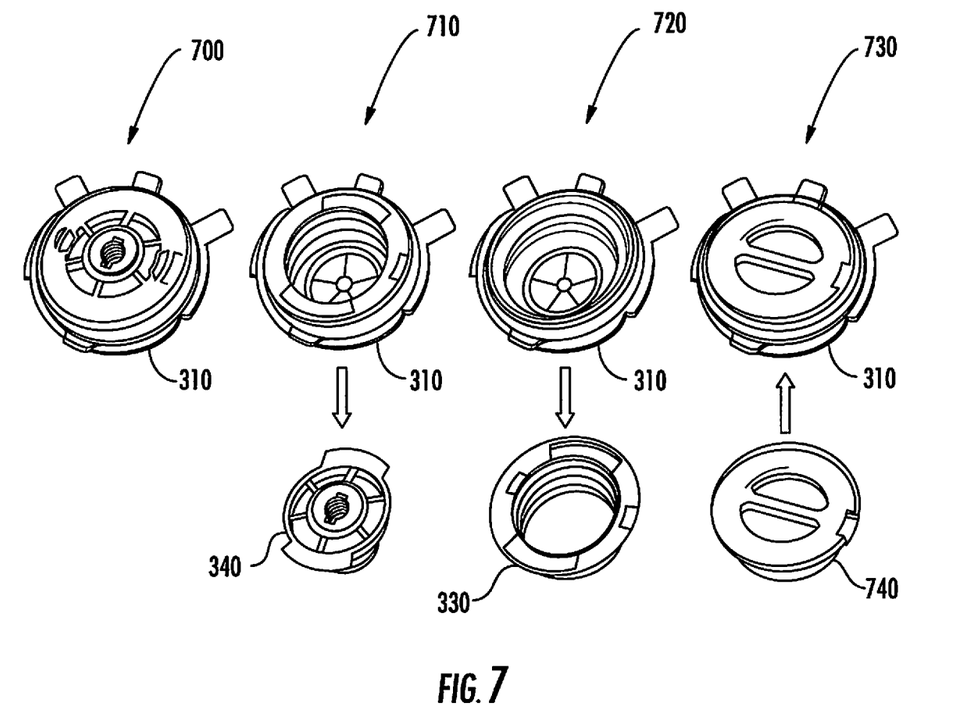
FIG. 7 depicts modes of operation for a respirator system in accordance with various embodiments.

Examples of various configurations of a respirator inlet assembly in accordance with various embodiments (e.g., respiratory inlet assembly 300) are depicted in FIG. 7. FIG. 7 depicts a first configuration 700, a second configuration 710, a third configuration 720, and a fourth configuration 730. One or more modes of operation may be performed for each configuration.

In the first configuration 710, both the adaptor 330 and the shut-off insert 340 are secured in place. In this configuration, the respiratory inlet assembly may accept (via an exterior mating surface of the respirator inlet assembly) a female fitting with a shut-off member (e.g., the supply fitting 360). For example, such a fitting may be used in conjunction with an APR supply system (e.g., first supply system 240).

The shut-off insert 340 may be released and removed from the adaptor 330 to place the respiratory inlet assembly in the second configuration 710. In the second configuration 710, the respirator inlet assembly may still accept a female fitting as in the first configuration 700; however, the shut-off functionality may not be achieved. With the shut-off insert 340 removed and the interior mating surface of the adaptor 332 thereby accessible, the respiratory inlet assembly may accept a male fitting. For example, the respiratory inlet assembly may accept a male fitting used in conjunction with a SCBA system (e.g., a male fitting of a demand valve) in the second configuration 710. Thus, the respiratory inlet assembly may operate interchangeably in two different modes in the second configuration 710, namely an APR mode (using a female fitting) and a SCBA mode (using a male fitting).

To provide the third configuration 720, the adaptor 330 may be removed from the cavity of the outer housing 310 to render the interior mating surface of the cavity of the outer housing 310 accessible. In the third configuration 720, as with the second configuration 710, the respirator inlet assembly may still accept a female fitting (without auto shut-off functionality). With the adaptor 330 removed and the interior mating surface of the cavity of the outer housing 320 thereby accessible, the respiratory inlet assembly may alternatively accept a male fitting that is larger than the male fitting accepted in the second configuration 710. For example, the respiratory inlet assembly may accept a male fitting used in conjunction with a PAPR or APR system (e.g., a male fitting) in the third configuration 720. For example, the respiratory inlet assembly may be configured to accept a canister filter of a PAPR assembly having a NATO DIN40 thread, or a canister filter of an APR assembly having a similar thread. Thus, the respiratory inlet assembly may operate interchangeably in three different modes in the third configuration 720, namely a first APR mode (using a female fitting), a PAPR mode (using a male fitting), and a second APR mode (using a male fitting and a different type of canister than the first APR mode).

In some modes of operation, one or more respiratory inlets may not be utilized. An exposed cavity, however, may present undesired opportunities for the ingress or collection of contaminants or hazardous materials. In some embodiments, a blanking structure is provided to fill or otherwise block the cavity when the respiratory inlet assembly is not actively used in conjunction with the supply of air for breathing. In the embodiment depicted in FIG. 7, the fourth configuration 730 is achieved by adding a blank insert 740 to the respiratory inlet assembly. The blank insert 740 is configured to substantially block the cavity of the outer housing 310 from contaminants in a surrounding atmosphere, and is configured to be releasably securable to the cavity. For example, one or both of the blank insert 740 and the cavity may include one or more of a latch, spring, clip, guide, tab, slot, or groove configured to releasably secure the blank insert 740 in the cavity of the outer housing 310. The respiratory inlet assembly may operate in a blank or idle mode of operation in the fourth configuration 740.

Thus, various embodiments provide a modular or otherwise switchable or interchangeable inlet assembly allowing for convenient switching between various modes of operation or types of fittings of air supply systems. Various embodiments provide one or more of improved convenience in switching between modes or types of air supply, reduction in the ingress of air or potential contaminants into a mask during switching of modes or types of air supply, or improved safety and versatility of respirator systems for CBRN or other hazardous applications.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter described herein without departing from its scope. While the dimensions and types of materials described herein are intended to define the parameters of the subject matter described herein, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the subject matter described herein, and also to enable any person skilled in the art to practice the embodiments of the subject matter described herein, including making and using any devices or systems and performing any incorporated methods. The patentable scope of the subject matter described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A respiratory inlet apparatus configured for securement to a mask, the respiratory inlet apparatus comprising:
   a housing including a mask end configured to be secured to the mask, and a fitting end configured to mate with a supply fitting of an air supply system;
   an exterior mating surface disposed on the fitting end, the exterior mating surface being configured as a male fitting surface to matingly accept a first type of air supply fitting configured as a female fitting, the respiratory inlet apparatus being configured to operate in a first mode when the female fitting of the first type of air supply fitting is mated to the male fitting of the fitting end of the housing;
   a cavity disposed within the housing having an opening oriented toward the fitting end, the cavity of the housing including an interior mating surface configured as a female fitting to matingly accept a second type of air supply fitting having an exterior mating surface configured as a male fitting, the respiratory inlet apparatus being configured to operate in a second mode when the male fitting of the second type of air supply fitting is mated to the female fitting of the cavity of the housing;
   an automatic shut-off member disposed within the cavity of the housing;
   an adaptor configured to be releasably secured in the cavity of the housing, the adaptor including an adaptor cavity having an interior mating surface configured to matingly accept a third type of air supply fitting, the respiratory inlet apparatus being configured to operate in a third mode when the third type of air supply fitting is mated to the interior mating surface of the adaptor cavity; and
   an automatic shut-off insert configured to be releasably secured in the adaptor cavity, the automatic shut-off insert being configured to cooperate with the automatic shut-off member to prevent flow of air through the adaptor cavity in a closed state and to allow flow of air through the adaptor cavity in an open state.

2. The respiratory inlet apparatus of claim 1, wherein the automatic shut-off member configured to accept a portion of the second type of air supply fitting.

3. The respiratory inlet apparatus of claim 2, wherein the automatic shut-off insert includes a latch member disposed proximate an external surface of the automatic shut-off insert, the latch member configured to releasably secure the automatic shut-off insert in the adapter cavity.

4. The respiratory inlet apparatus of claim 1, wherein the first type of air supply fitting is configured to provide air from a first type of filter, wherein the second type of air supply fitting is configured to provide air from a self-contained breathing apparatus (SCBA), and wherein the third type of air supply fitting is configured to provide air from a second type of filter.

5. The respiratory inlet apparatus of claim 1, wherein:
   the automatic shut-off member includes a first shut-off surface; and
   the automatic shut-off insert includes:
      a shut-off opening configured to accept a portion of the first type of air supply fitting; and
      an insert shut-off member having a second shut-off surface, the first shut-off surface being configured to cooperate with the second shut-off surface, the insert shut-off member being actuated by movement of the first type of supply fitting when the first type of supply fitting is engaged with the shut-off opening.

6. The respiratory inlet apparatus according to claim 5, further comprising a blank insert configured to be accepted by the cavity of the housing, the blank insert configured to substantially block the cavity from an atmosphere surrounding the respiratory inlet apparatus.

7. The respiratory inlet apparatus according to claim 6, further comprising an inlet valve interposed between the cavity and the fitting end, the inlet valve configured to control a flow of air through the respiratory inlet apparatus.

8. The respiratory inlet apparatus according to claim 1, wherein the first type of air supply fitting is configured to provide air from a filter, and wherein the second type of air supply fitting is configured to provide air from a SCBA self-contained breathing apparatus (SOBA).

9. A respiratory inlet assembly configured for securement to a mask, the respiratory inlet assembly comprising:
    a respiratory inlet housing having a mask end configured to be secured to the mask, and a fitting end configured to mate with a supply fitting of an air supply system, the respiratory inlet housing including:
        an exterior mating surface disposed on the fitting end, the exterior mating surface having a threading and being configured as a male fitting to matingly accept a first type of air supply fitting having a threading and configured as a female fitting, the threading of the exterior mating surface of the respiratory inlet housing being complementary to the threading of the first type of air supply fitting; and
        a cavity disposed within the respiratory inlet housing having an opening oriented toward the fitting end, the cavity having an interior mating surface having a threading and being configured as a female fitting to matingly accept a second type of air supply fitting having a threading and configured as a male fitting, the threading of the interior mating surface of the cavity being complementary to the threading of the second type of air supply fitting;
    an automatic shut-off member disposed within the cavity of the respiratory inlet housing, the automatic shut-off member including a first shut-off surface;
    an adaptor formed as a generally annular member and being configured to be releasably secured within the cavity of the respiratory inlet housing, the adaptor including an adaptor cavity, an adaptor interior mating surface, and an adaptor exterior mating surface having a threading, the adaptor cavity passing through the adaptor, the adaptor exterior mating surface extending circumferentially around the adaptor and the adaptor interior mating surface being within the adaptor cavity, the adaptor cavity and the adaptor interior mating surface being configured to matingly accept a third type of air supply fitting, the threading of the adaptor exterior mating surface being complementary to the threading of the interior mating surface of the cavity of the respiratory inlet housing; and
    an automatic shut-off insert configured to be releasably secured within the adaptor cavity, the automatic shut-off insert configured to cooperate with the automatic shut-off member to prevent flow of air through the adaptor cavity in a closed state and to allow flow of air through the adaptor cavity in an open state, the automatic shut-off member including a shut-off opening and a second shut-off surface, the first shut-off surface being configured to cooperate with the second shut-off surface, the shut-off member being actuated by movement of the first type of supply fitting when the first type of supply fitting is engaged with the shut-off opening.

10. The respiratory inlet assembly of claim 9, wherein the automatic shut-off insert includes a latch member disposed proximate an external surface of the automatic shut-off insert, the latch member configured to releasably secure the automatic shut-off insert in the one of the adaptor cavity or the cavity of the respiratory inlet housing.

11. The respiratory inlet assembly of claim 10, further comprising a blank insert configured to be accepted by the cavity of the respiratory inlet housing, the blank insert configured to substantially block the cavity of the respiratory inlet housing from an atmosphere surrounding the respiratory inlet housing.

12. The respiratory inlet assembly of claim 11, wherein the first type of air supply fitting is configured to provide air from a first type of filter during a first mode of operation of the mask, wherein the second type of air supply fitting is configured to provide air from a self-contained breathing apparatus (SCBA) during a second mode of operation of the mask, and wherein the third type of air supply fitting is configured to provide air from a second type of filter during a third mode of operation of the mask.

13. The respiratory inlet assembly of claim 12, further comprising an inlet valve interposed between the cavity of the respirator inlet and the fitting end, the inlet valve configured to control a flow of air through the respiratory inlet housing.

14. A respirator assembly comprising:
    a mask comprising an inlet port; and
    a respiratory inlet apparatus configured to be accepted by the inlet port, the respiratory inlet apparatus including:
        a housing having a mask end configured to be secured to the mask, and a fitting end configured to mate with a supply fitting of an air supply system;
        an exterior mating surface disposed on the fitting end, the exterior mating surface being configured as a male fitting surface to matingly accept a first type of air supply fitting configured as a female fitting, the respiratory inlet apparatus being configured to operate in a first mode when the female fitting of the first type of air supply fitting is mated to the male fitting of the fitting end of the housing;
        a cavity disposed in the housing having an opening oriented toward the fitting end, the cavity of the housing comprising an interior mating surface configured as a female fitting to matingly accept a second type of air supply fitting having an external mating surface configured as a male fitting, the respiratory inlet apparatus being configured to operate in a second mode when the male fitting of the second type of air supply fitting is mated to the female fitting of the cavity of the housing;
        an automatic shut-off member disposed within the cavity of the housing;
        an adaptor configured to be releasably secured in the cavity of the housing, the adaptor including an adaptor cavity having an interior mating surface configured to matingly accept a third type of air supply fitting, the respiratory inlet apparatus being configured to operate in a third mode when the third type of air supply fitting is mated to the interior mating surface of the adaptor cavity; and an automatic shut-off insert configured to be releasably secured in the adaptor cavity, the automatic shut-off insert being configured to cooperate with the automatic shut-off member to prevent flow of air through the adaptor cavity in a closed state and to allow flow of air through the adaptor cavity in an open state.

15. The respirator assembly of claim 14, wherein the first type of air supply fitting is configured to provide air from a first type of filter, wherein the second type of air supply fitting is configured to provide air from a self-contained breathing apparatus (SCBA), and wherein the third type of air supply fitting is configured to provide air from a second type of filter.

16. The respirator assembly of claim 14, wherein:
the automatic shut-off member includes a first shut-off surface; and
the automatic shut-off insert includes:
an insert shut-off opening configured to accept a portion of the first type of air supply fitting; and
an insert shut-off member having a second shut-off surface, the insert first shut-off surface being configured to cooperate with the second shut-off surface, the insert shut-off member being actuated by rotation of the first type of supply fitting when the first type of supply fitting is engaged with the shut-off opening.

17. The respirator assembly of claim 16, further comprising a blank insert configured to be accepted by the cavity of the housing, the blank insert configured to substantially block the cavity of the respiratory inlet apparatus from an atmosphere surrounding the respiratory inlet apparatus.

* * * * *

UNITED STATES PATENT AND TRADEMARK OFFICE
CERTIFICATE OF CORRECTION

PATENT NO. : 10,507,341 B2
APPLICATION NO. : 14/854328
DATED : December 17, 2019
INVENTOR(S) : Graham Langford Page 1 of 1

It is certified that error appears in the above-identified patent and that said Letters Patent is hereby corrected as shown below:

In the Claims

Column 16
Line 55, in Claim 4, after "filter," delete "wherein".
Line 57, in Claim 4, after "and" delete "wherein".

Column 17
Line 16, in Claim 8, after "and" delete "wherein".
Line 18, in Claim 8, delete "(SOBA)." and insert -- (SCBA). -- therefor.

Column 18
Line 22, in Claim 12, after "mask," delete "wherein".
Line 25, in Claim 12, after "and" delete "wherein".

Column 19
Line 18, in Claim 16, delete "an insert" and insert -- a -- therefor.
Line 21, in Claim 16, after "the" delete "insert".

Signed and Sealed this
Eleventh Day of February, 2020

Andrei Iancu
*Director of the United States Patent and Trademark Office*